(12) United States Patent
Kobayashi (10) Patent No.: US 6,638,215 B2
(45) Date of Patent: Oct. 28, 2003

(54) VIDEO ENDOSCOPE SYSTEM (75) Inventor: Hiroyuki Kobayashi, Tokyo (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/933,110

(22) Filed: Aug. 21, 2001

(65) Prior Publication Data

US 2002/0026098 A1 Feb. 28, 2002

(30) Foreign Application Priority Data

Aug. 25, 2000 (JP) ........................................ 2000-256168

(51) Int. Cl.$^7$ .............................. A61B 1/06; A61B 6/00
(52) U.S. Cl. .................... 600/160; 600/178; 600/181
(58) Field of Search ........................ 600/100, 178–182, 600/160, 477, 478; 348/68–70; 362/574; 250/458.1, 484.2, 461.2

(56) References Cited

U.S. PATENT DOCUMENTS 5,749,830 A * 5/1998 Kaneko et al. ............. 600/160
6,364,829 B1 * 4/2002 Fulghum .................... 600/160

* cited by examiner

Primary Examiner—John Mulcahy
(74) Attorney, Agent, or Firm—Greenblum & Bernstein, P.L.C.

(57) ABSTRACT

White light emitted from a first light source is sequentially converted into green light, blue light, and red light by a first wheel. Excitation light emitted from a second light source passes through a second wheel. The green light, the blue light and the red light, and the excitation light are switched by shutters to enter a prism. The optical path of the green light, the blue light and the red light transmitted through the prism coincides with the optical path of the excitation light reflected by the prism. As a result, the green light, the blue light, the red light and the excitation light sequentially and repeatedly enter a light guide.

6 Claims, 9 Drawing Sheets

VIDEO ENDOSCOPE SYSTEM

BACKGROUND OF THE INVENTION

1. Field of the Invention

The present invention relates to a video endoscope system that photographs images of body cavities using autofluorescence from living tissue to generate image data which is to be used to determine whether the tissue is normal or abnormal. The present disclosure relates to subject matter contained in Japanese Patent Application No. 2000-256168 (filed on Aug. 25, 2000) which is expressly incorporated herein by reference in its entirety.

2. Description of the Related Art

Recently, video endoscope system capable of observing fluorescence (autofluorescence) emitted from living tissue irradiated with a predetermined wavelength of excitation light are used. These video endoscope devices comprise a light source devices for emitting both visible light and excitation light that excites living tissue to cause autofluorescence. This excitation light is typically ultraviolet light. The living tissue irradiated with this excitation light emits autofluorescence. The intensity of the fluorescence generated by healthy tissue is stronger than that generated by unhealthy tissue. A video endoscope system of this kind irradiates living tissue with excitation light emitted from a light source device, creates a fluorescent image based on the intensity distribution of autofluorescence emitted from the living tissue to be displayed on a monitor. Note that in this fluorescence image, normal tissue appears bright, while diseased tissue appears dark. An operator observes the fluorescence image and determines portions darker than other portions in the fluorescence image as diseased tissue. However, the dark portions in a fluorescence image do not always indicate diseased tissue. For example, undulant shape of the tissue itself and a forceps projecting from the distal end of the endoscope forms shadows in the body cavity, which are indicated as dark portions in the fluorescent image. Thus, shaded portions are not easily distinguished from diseased portions.

Therefore, a video endoscope system which generates diagnostic images in which diseased areas are distinguished from shaded portions is proposed. A light source device of this video endoscope system sequentially and repeatedly emits green light, blue light, red light, a reference light that is visible light of a predetermined wavelength, and excitation light. The emitted light is guided into the body cavity of a patient through a light guide installed in the video endoscope to irradiate living tissue. An objective optical system installed in the video endoscope forms images of the object from the green light, the blue light, and the red light, respectively, during the period when the light source device emits the green light, during the period when it emits the blue light, and during the period when it emits the red lights. The images are converted into image signals by a CCD installed in the video endoscope. The image signals are synthesized into a color image by a processor of the video endoscope system.

On the other hand, the objective optical system forms a reference image of the object from the reference light during the period in which the light source device emits the reference light. Also, the objective optical system forms an autofluorescence image of living tissue during the period in which the light source device emits the excitation light. These reference and autofluorescence images are converted into image signals by the CCD, and the image signals are input to the processor. The process or subtracts the image signal obtained from the reference light from the image signal obtained from the autofluorescence to extract only portions from which only weak fluorescence is generated due to abnormalities. Furthermore, the processor sets these portions extracted from the fluorescence image signal to a predetermined color and superposes them on the color image to create a diagnostic image. In this diagnostic image, the operator can distinguish diseased portions from the shaded portions and easily recognize the locations of the diseased areas.

Figure 8:
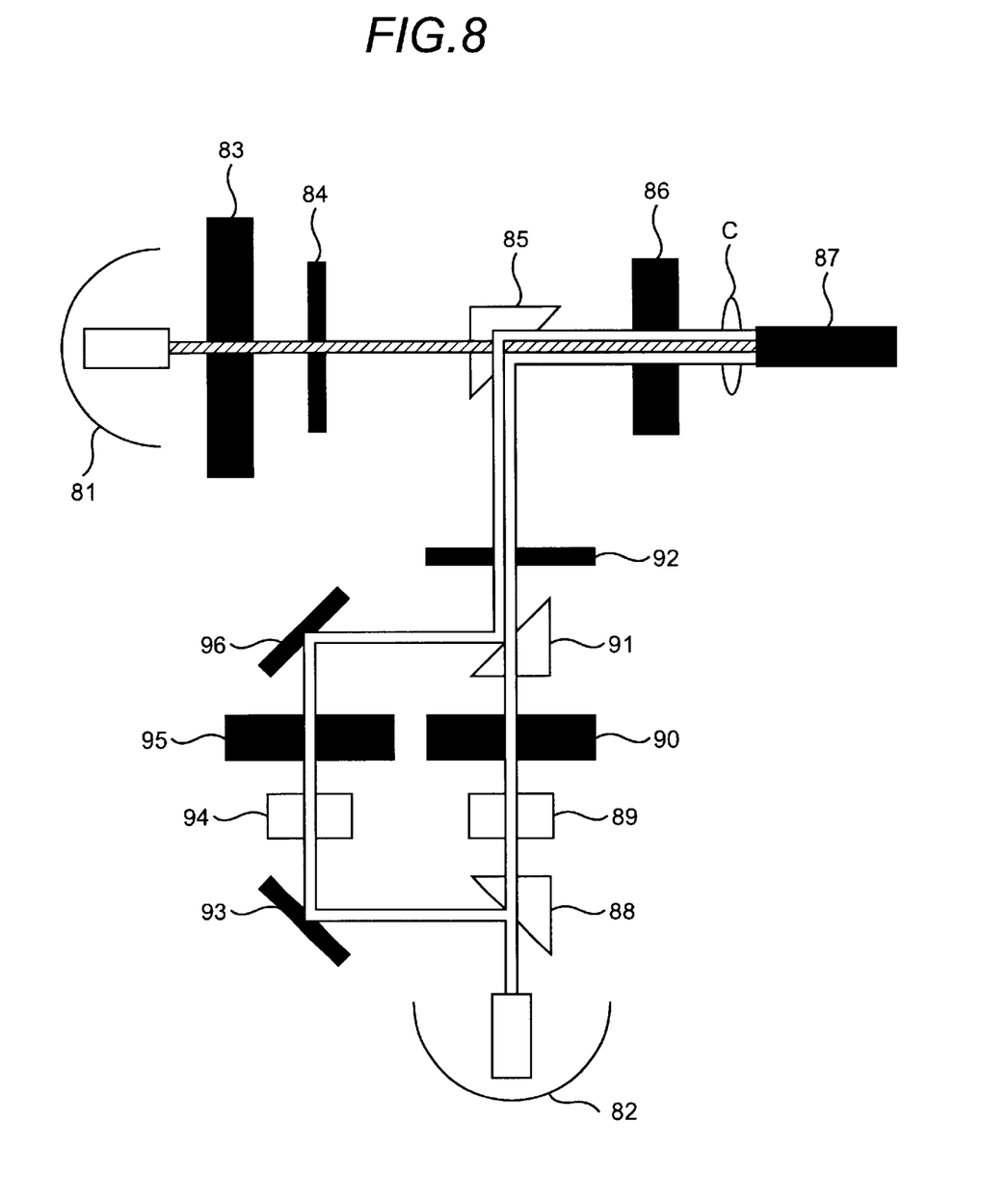
FIG. 8 is a schematic illustration showing the optical configuration of a conventional light source device.
Figure 9A:
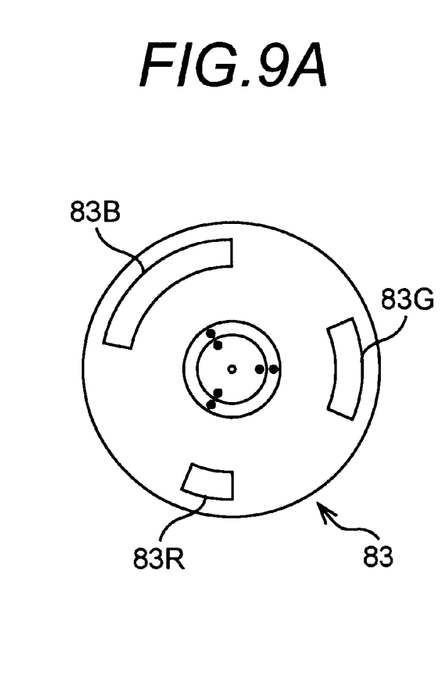
FIGS. 9A, 9B, and 9C are front views of conventional wheels.

The light source device for this video endoscope system will be described in further detail, referring to FIG. 8. The light source device has a first light source 81 for emitting white light and a second light source 82 for emitting light containing the components of the spectra of the excitation light and reference light. A first wheel 83, a first shutter 84, a prism 85, a diaphragm 86, and a condenser lens C are arranged along the optical path of white light emitted from the first light source 81, in order. As shown in FIG. 9A, the first wheel 83 is a disk, with three openings formed along its circumference. These openings are fitted with a green filter 83G, a blue filter 83B, and a red filter 83R to transmit green light, blue light, and red light, respectively. The first wheel 83 is joined to a motor (not shown) and driven to rotate by this motor. The first wheel 83 is disposed at a location where the filters 83G, 83B, and 83R are sequentially inserted into the optical path of the white light emitted from the first light source 81, with its rotation. The white light emitted from the first light source 81 is sequentially converted into green light, blue light, and red light by the filters 83G, 83B, and 83R of the first wheel 83. The converted light advances to the first shutter 84. This shutter 84 can block incident light or allow it to pass therethrough. The light which passed through the first shutter 84 is then transmitted through the first prism 85 and enters the diaphragm 86 which adjusts amount of the light. The light is then converged by the condenser lens C on the proximal end of the light guide 87.

Figure 9B:
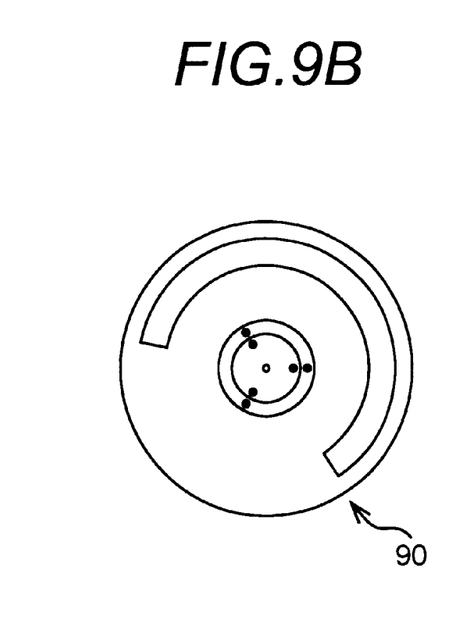

A second prism 88 is disposed on an optical path of light emitted from the second light source 82. The light emitted from the second light source 82 is split into transmitted light and reflected light by the second prism 88. An excitation light filter 89, a second wheel 90, a third prism 91, and a second shutter 92 are arranged along the optical path of the light transmitted through the second prism 88, in order. The light transmitted through the second prism 88 then enters the excitation light filter 89, which extracts and transmits only those components corresponding to the excitation light from the incident light. The transmitted excitation light then enters the second wheel 90. As shown in FIG. 9B, the second wheel 90 is a disk, with one opening formed along its circumference. This opening is fitted with a transparent member to transmit the excitation light. The second wheel 90 is joined to a motor (not shown) and driven to rotate by this motor. The second wheel 90 is disposed at a location where the opening is periodically inserted into the optical path of the excitation light. The excitation light is then transmitted through the third prism 91 and advances to the second shutter 92. The second shutter 92 can block the incident light or allow it to pass therethrough. The light which passed through the second shutter 92 is then reflected by the first prism 85, and thereafter travels along the same optical path as the green light, the blue light and the red light as described above, and finally enters the light guide 87.

A first mirror 93, a reference light filter 94, a third wheel 95, and a second mirror 96 are arranged along the optical path of the light reflected by the second prism 88, in order.

Figure 9C:
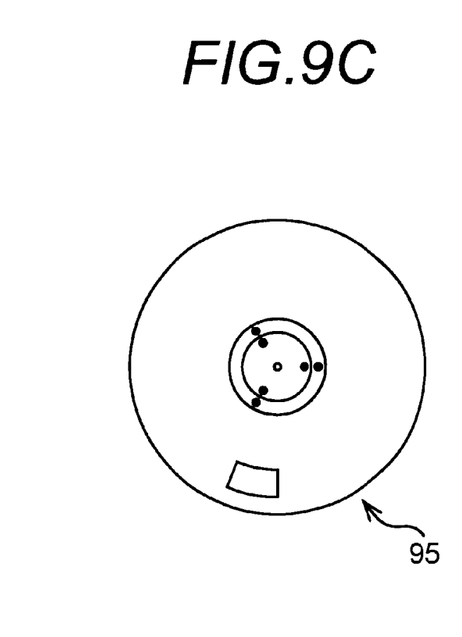

The light reflected by the second prism 88 is further reflected by the mirror 93, then enters the reference light filter 94, which extracts and transmits only the components corresponding to the reference light from the incident light. The transmitted reference light then enters the third wheel 95. As shown in FIG. 9C, the third wheel 95 is a disk, with one opening formed along its circumference. This opening is fitted with a transparent member to transmit the reference light. The third wheel 95 is connected to a motor (not shown) and driven to rotate by this motor. The third wheel 95 is disposed at a location where the opening is periodically inserted into the optical path of the reference light. The reference light is then reflected by the second mirror 96, further reflected by the third prism 91, and thereafter travels along the same optical path as the excitation light described above to enter the light guide 87 finally.

The third wheel 95 allows the reference light to pass therethrough only when the second wheel 90 blocks the excitation light. Besides, while the first shutter 84 transmits the green, blue, or red light, the second shutter 92 blocks the excitation light and the reference light. In contrast, while the second shutter transmits the excitation light or reference light, the first shutter 84 blocks the green, blue, and red lights. After the first shutter 84 has passed each of the green light, blue light and red light once, the second shutter 92 passes each of the excitation light and reference light once. Thus, the green light, the blue light, the red light, the excitation light and the reference light are sequentially and repeatedly incident upon the light guide 87. The light incident on the light guide 87 is guided by the light guide 87 itself and emitted toward an object. The object is thus sequentially and repeatedly irradiated by the green light, the blue light, the red light, the excitation light and the reference light.

Thus, in such a video endoscope system, the light source device must sequentially and repeatedly introduce the green light, the blue light, the red light, the excitation light and the reference light into the light guide 87. Accordingly, the optical system of the light source device has a complex configuration, incorporating the above described three prisms. Such a complex optical system attenuates amount of light entering the light guide 87. Since the resulting autofluorescence from living tissue is faint, autofluorescence of the intensity required for observation cannot be obtained without the application of excitation light of a sufficient intensity. The conventional light source device is incapable of emitting excitation light of a sufficient intensity, failing to cause autofluorescence of the required intensity. Further, a complex optical system requires additional manufacturing steps as well as time and labor to align the optical axis of each optical member, making it difficult to keep down product costs.

SUMMARY OF THE INVENTION

It is an object of the present invention to provide a video endoscope system including a light source device that can emit various types of irradiating light with a simple configuration.

To attain this object, first aspect of the video endoscope system has a visible light source for emitting visible light, an excitation light source for emitting excitation light that excites living tissue to cause autofluorescence, which is arranged so that the emitted excitation light crosses, at a predetermined intersecting point, to an optical path of the visible light emitted by said visible light source, a light guide for guiding light to irradiate an object, an optical member disposed at the intersecting point to guide the visible light and the excitation light to the light guide along same optical path, a switching mechanism for switching between the visible light and the excitation light to introduce them in to the optical member, an objective optical system for converging the components of light from a surface of the object irradiated with the light guide other than the excitation light, to form an image of the surface of the object, and an imaging device for picking up the image to convert it into an image signal. A processor controls the switching mechanism to alternately and repeatedly introduce the visible light and excitation light into the light guide, generates normal image data on the basis of a portion of the image signal corresponding to a period during which the visible light is introduced into the light guide, generates fluorescence image data on the bases of a portion of the image signal corresponding to a period during which the excitation light is introduced into the light guide, obtains reference image data from said normal image data, extracting a diseased portion on the basis of the reference image data and the fluorescence image data and superimposes the diseased portion on the normal image data to generate diagnostic image data to be displayed as a moving picture.

This configuration enables the reference image data to be obtained from normal image data without a separate optical system emitting the reference light. Therefore, the video endoscope system can generate diagnostic image data on the bases of the reference image data with a simple illumination optical system through which the excitation light does not attenuate.

Note that the switching mechanism may be a prism or a dichroic mirror for coupling the optical path of the visible light and that of the excitation light together, and shutters that can block the visible and the excitation lights respectively. The switching mechanism may alternatively be a switching mirror that is inserted into and retracted from the intersecting point.

Further, second aspect of the video endoscope system according to the present invention has a light source for emitting light containing components of a spectrum of visible light and components of a spectrum of excitation light that excites living tissue to cause autofluorescence, a light guide for guiding light to irradiate an object, a separation device for separating the light emitted from the light source into components of the spectrum of the visible light and the components of the spectrum of the excitation light, a light guiding optical system for separately guiding the visible light and the excitation light so that they cross each other at a predetermined intersecting point, an optical member disposed at the intersecting point to guide the visible light and the excitation light to the light guide, a switching mechanism for switching between the visible light and the excitation light to introduce them into the light guide, an objective optical system for converging those components of light from a surface of the object irradiated with the light guide other than the excitation light to form an image of the surface of the object, and an imaging device for picking up the image to convert it into an image signal. A processor controls the switching mechanism to alternately and repeatedly introduce the visible light and the excitation light into said light guide, generates normal image data on the bases of a portion of the image signal corresponding to a period during which the visible light is introduced into the light guide, generates the fluorescence image data on the bases of a portion of the image signal corresponding to a period during which the excitation light is introduced into the light guide, obtains reference image data from the normal image data, subtracts a diseased portion on the bases of the reference image data and the fluorescence image data, and superimposes the diseased portion on the normal image data to generate diagnostic image data to be displayed as a moving picture.

This configuration allows the visible light and the excitation light to be obtained from light emitted by the single light source, so that the visible light and the excitation light sequentially and repeatedly enters the light guide. The separation device may be a dichroic mirror or a prism.

Further, the visible light may be sequentially converted into green light, blue light, and red light by a wheel inserted into the optical path of the visible light. In this case, the object is sequentially and repeatedly irradiated with the green light, the blue light, the red light and the excitation light. The imaging device then converts an image of the subject, sequentially and repeatedly irradiated with the green light, the blue light, the red light and the excitation light, into an image signal. The processor then processes this image signal to obtain normal image data and a fluorescence image data. The processor may also generate reference image data on the basis of an image signal obtained by the imaging device while the objects is illuminated by the red light.

DESCRIPTION OF THE PREFERRED EMBODIMENTS

Embodiments of a video endoscope device according to the present invention will be described below with reference to the drawings.

First Embodiment

Figure 1:
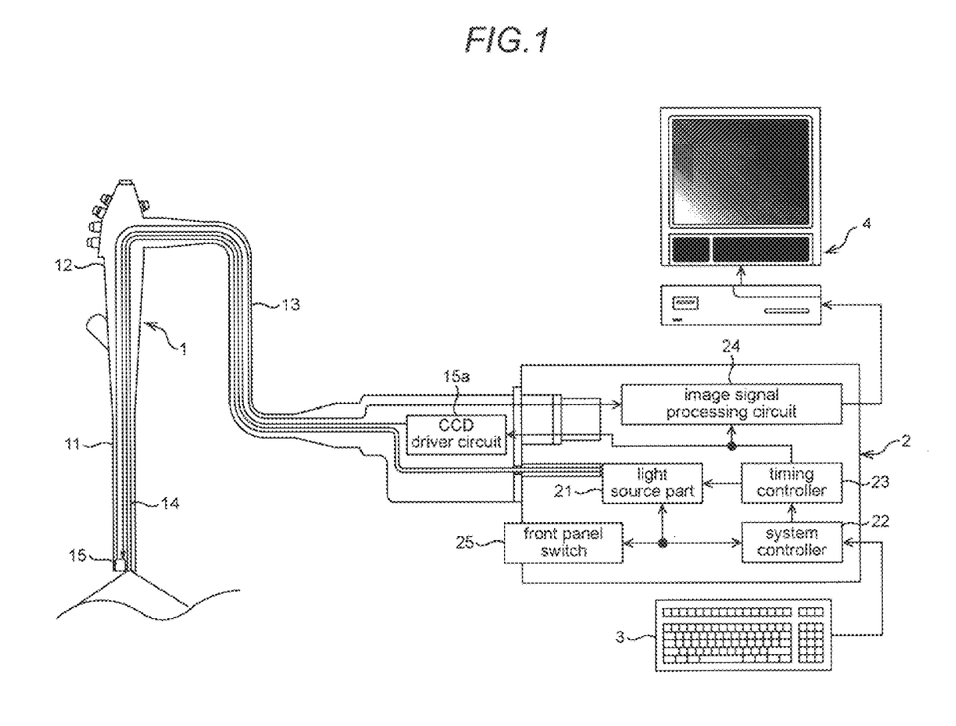
FIG. 1 is a schematic illustration showing the structure of a video endoscope system according to a first embodiment of the present invention.

FIG. 1 is a schematic illustration showing the structure of a video endoscope system according to the first embodiment. As shown in FIG. 1, this video endoscope system consists of a video endoscope 1, an external device (processor) 2, an input device 3 and a display device 4.

The video endoscope 1 has a insertion part 11 that is formed as a flexible tube and that is to be inserted into living body, an operating section 12 integrally joined to a proximal end of the insertion part 11, and a light-guide flexible tube 13 integral joined to the operating section 2 and detachably connected to the external device 2. The insertion part 11 has a bending mechanism (not shown) incorporated into a predetermined area near its tip, which is bent when a dial provided on the operating section 12 is operated. The insertion part 11 is incorporated with a tip member (not shown)made of a hard material at a distal end thereof. The tip member is formed with at least three through-holes drilled therein, two of which are provided with a light distribution lens and an objective lens (not shown), with the remainder used as a forceps channel. The operating section 12 has various operation switches in addition to a dial. The video endoscope 1 also has a light guide fiber bundle (hereafter referred to as a "light guide") composed of a large number of bundled multimode optical fibers. The light guide 14 is led through the insertion part 11, the operating section 12 and the light-guide flexible tube 13 so that its distal end face is opposite the light distribution lens. The light-guide flexible tube 13 has one end connected to the operating section 12, with the other end constituting a connector. A circuit in the video endoscope 1 is connected to a circuit in the external device 2 when the connector of the light-guide flexible tube 13 is fitted to a socket of the external device 2. A proximal end of the light guide 14 is led through a guide pipe projecting from a joining surface of the connector. Accordingly, if the connector is connected to the socket of the external device 2, the proximal end of the light guide 14 is inserted into the external device 2. The video endoscope 1 also has a CCD (Charge-Coupled Device) 15 as an imaging device incorporated in the tip member. An imaging surface of the CCD 15 is disposed at a position on which the objective lens (not shown) forms an image of the object when the distal end of the video endoscope 1 is located opposite the object. In addition, an excitation light cut-off filter (not shown) is set on an optical path from the objective lens to the CCD 15. The excitation light cut-off filter blocks light of the predetermined wavelength spectrum used as excitation light for exciting living tissue to cause autofluorescence. The objective lens and the excitation light cut-off filter correspond to an objective optical system. Further, in the connector of the light-guide flexible tube 13 is installed a CCD driver circuit 15a, which is connected to the CCD 15 through a signal line.

The external device 2 comprises a light source part 21, a system controller 22, a timing controller 23, an image signal processing circuit 24 and a front panel switch 25. The light source part 21 is arranged so as to face the proximal end face of the light guide 14 to introduce illuminating light into it, when the connector is joined to its socket. The internal configuration of the light source part 21 is described further below. These system controller 22, timing controller 23, CCD driver circuit 15a and image processing circuit 24 correspond to a main circuit of the processor. The system controller 22 is connected to each of the light source part 21, the timing controller 23, the front panel switch 25 and the input device 3, and controls the light source part 21 and the timing controller 23 according to set condition obtained through the front panel switch 25 and the input device 3. The timing controller 23 is connected to the light source part 21 and the image signal processing circuit 24, and generates reference signals required for various processes in the external device 2. The timing controller 23 is connected to terminals in the socket which can be electrically contacted to terminals (not shown) in the connector connected to the CCD driver circuit 15a. If the connector is joined to the socket, the CCD driver circuit 15a receives the reference signal output by the timing controller 23, generates a drive signal based on this reference signal, and transmits it to the CCD 15, and the CCD 15 then captures an image formed on its imaging surface and outputs an image signal in accordance with the drive signal. The image signal processing circuit 24 is connected to other terminals in the socket which can be electrically connected to terminals (not shown) in the connector connected to the CCD 15. When the connector is joined to the socket, the image signal processing circuit 24 is electrically connected to the CCD 15. The image signal processing circuit 24 is connected to the display device 4, that is a personal computer or a television monitor. The image signal processing section 24 receives the reference signal output by the timing controller 23 and obtains an image signal output by the CCD 15 on the basis of this reference signal. The image signal processing section 24 then processes the obtained image signal as described further below and causes it to be displayed on the display device 4.

Figure 2:
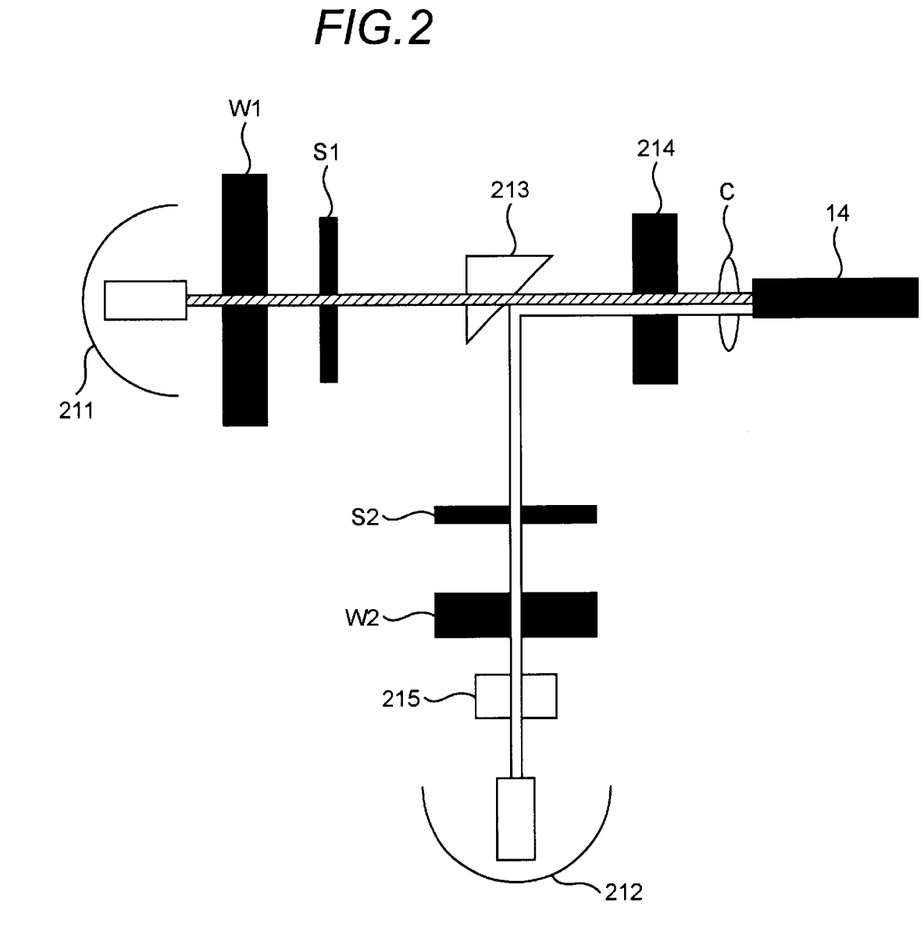
FIG. 2 is a schematic illustration showing the optical configuration of a light source device.
Figure 3A:
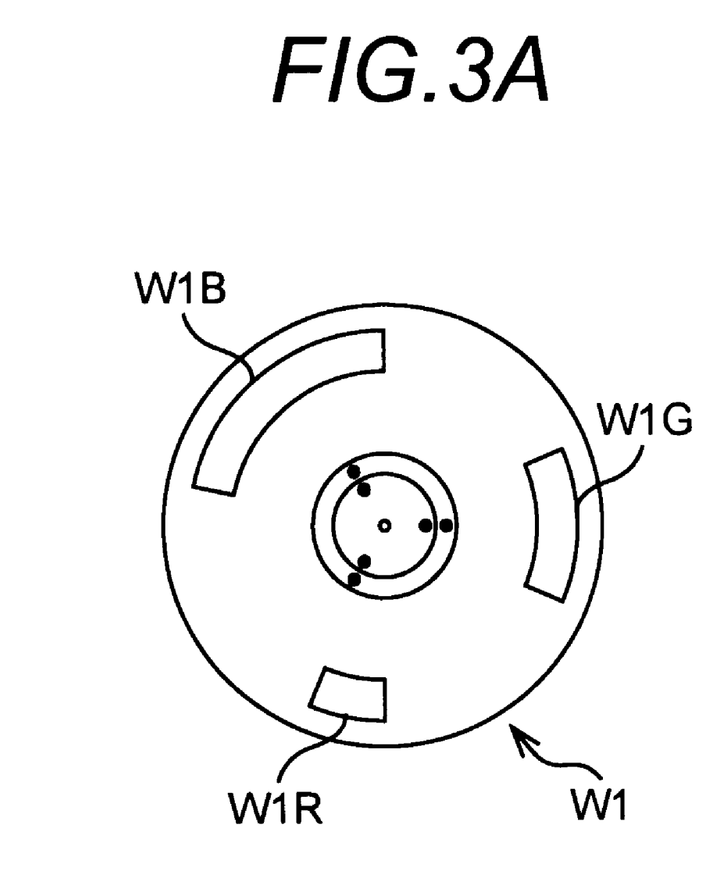
FIGS. 3A and 3B are front views of a first wheel and a second wheel, respectively.

Next, the configuration of the light source part 21 of the external device 2 will be described with reference to FIG. 2. The light source part 21 comprises a first light source 211 for emitting white light and a second light source 212 for emitting light containing components of a spectrum that is available as excitation light. First light source 211 corresponds to a visible light source, while the second light source corresponds to an excitation light source. A first wheel W1, a first shutter S1, a prism 213, a diaphragm 214, and a condenser lens C are arranged along the optical path of white light emitted from the first light source 211, in order. FIG. 3A is a front view of the first wheel W1. As shown in this figure, the first wheel W1 is a disk with three openings formed along its circumference. The openings are fitted with a green filter W1G transmitting only green light, a blue filter W1B transmitting only blue light, and a red filter W1R transmitting only red light, respectively. The first wheel W1 is joined to a motor (not shown) and driven to rotate by this motor. The first wheel W1 is disposed at a location where the filters W1G, W1B, and W1R are sequentially inserted into the optical path of white light emitted from the first light source 211 with its rotation by the motor. The white light emitted from the first light source 211 as collimated light is converted into green light, blue light, and red light in sequence by the filters W1G, W1B, and W1R of the first wheel W1. The light converted by the filters W1G, W1B and W1R advances to the first shutter S1. The first shutter S1 can block incident light or allow it to pass therethrough. The light which passed through the first shutter S1 is then enters the prism 213, which has a UV reflection film deposited on its inclined surface to transmit visible light, while reflecting the excitation light. Thus, the visible light (the green light, the blue light and the red light) passing through the prism 213 advances to the diaphragm 214. The light of which amount is adjusted to a proper quantity by the diaphragm 214 is converged onto the proximal end face of the light guide 14 by the condenser lens C.

Figure 3B:
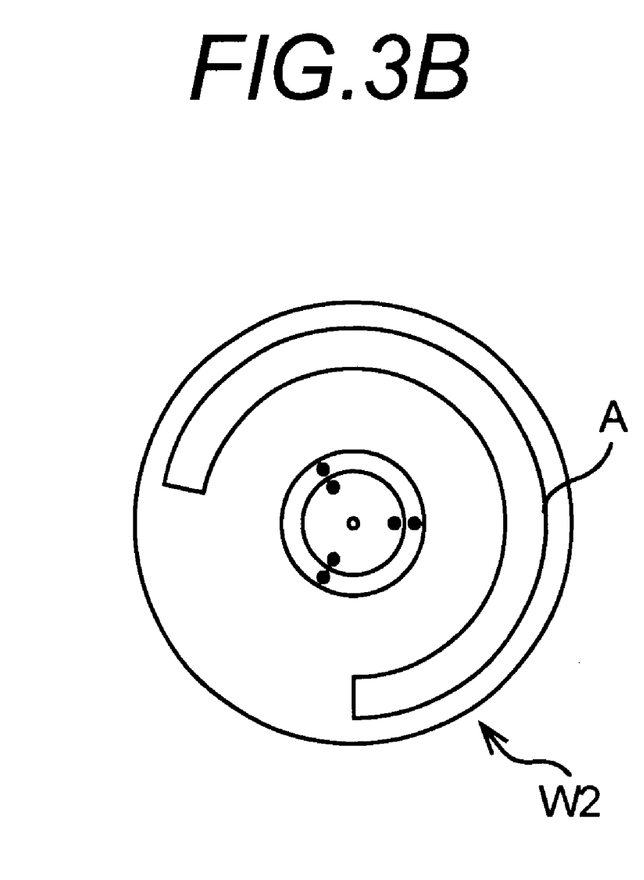

On the other hand, the second light source 212 is arranged so that the optical path of the light emitted from the second light source as collimated light orthogonally crosses to the optical path of the light passing through the first shutter S1 on the inclined surface of the prism 213. The prism 213 is arranged so that its inclined surface is inclined 45° to the optical path of the light passing through the first shutter S1 and to that of the light passing through the second shutter S2. An excitation light filter 215, the second wheel W2, and the second shutter S2 are arranged along the optical path of the light from the second light source 212 to the prism 213. The excitation light filter 215 extracts and transmits only the components of the excitation light from the light emitted from the second light source 212. The excitation light transmitted through the excitation light filter 215 then advances to the second wheel W2. As shown in FIG. 3B, the second wheel W2 is a disk, with a fan-shaped opening A formed along its circumference. The opening A is fitted with a transparent member transmitting the excitation light. In the example shown in FIG. 3B, the opening A in the second wheel W2 is formed over three-fourths of the circumference of the second wheel W2. The second wheel W2 is joined to a motor (not shown) and driven to rotate by this motor. The second wheel W2 is disposed at a location where the opening A is periodically inserted into the optical path of the excitation light. The excitation light transmitted through the opening A in second wheel W2 then advances to the second shutter S2, which can block incident excitation light or allow it to pass therethrough. The excitation light which passed through the second shutter S2 is then reflected by the prism 213, and thereafter travels along the same optical path as the green light, the blue light and the red light, as described above, finally entering the light guide 14.

Figure 4:
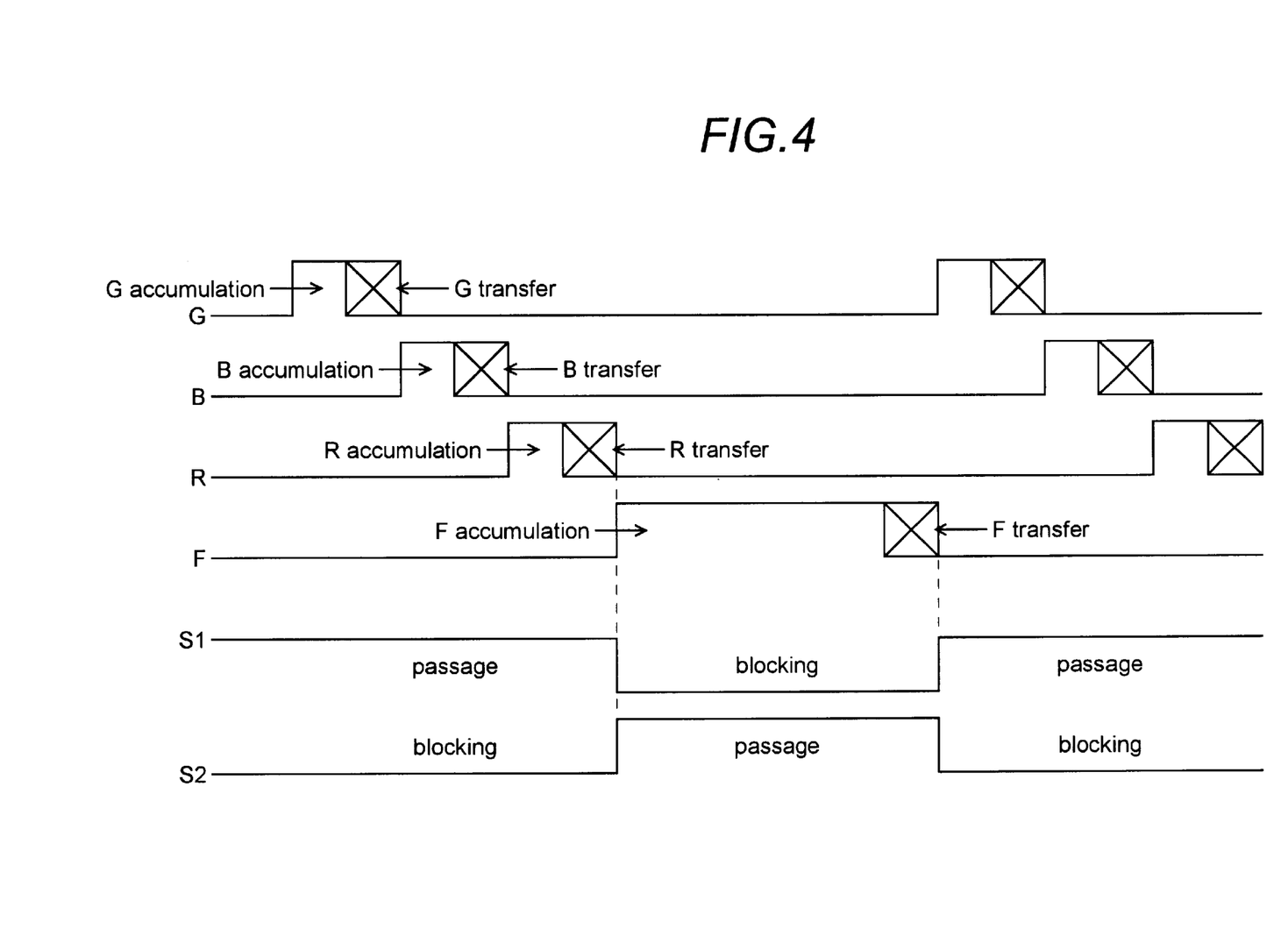
FIG. 4 is a timing chart showing operations of the light source device and a CCD.

The motors joined to the wheels W1 and W2, respectively, and the shutters S1 and S2 are connected to the timing controller 23 via signal lines (not shown). The wheels W1 and W2 and the shutters S1 and S2 operate based on the reference signals output by the timing controller 23. The shutters S1 and S2 correspond to a switching mechanism. FIG. 4 is a timing chart showing the timings at which the light source part 21 and the CCD 15 operate. The wheels W1 and W2 of the light source part 21 rotate at constant angular speed. While the first wheel W1 rotates once, the filters W1G, W1B and W1R are sequentially inserted into the optical path of the white light emitted from the first light source 211, so that the white light is sequentially converted into the green light, the blue light and the red light, which then advance to the first shutter S1. While the first wheel W1 rotates once, the second wheel W2 also rotates once in synchronism therewith. While the second wheel W2 rotates once, its opening A is inserted once into the optical path of the excitation light transmitted through the excitation light filter 215, so that the excitation light passes through the opening A in second wheel W2 to advance to the second shutter S2 only for a predetermined period shorter than the revolution of the second wheel W2. In other words, since the second wheel S2 rotates once while the first wheel W1 rotates once, the green light, the blue light and the red light sequentially enter the first shutter S1, whereas the excitation light enters the second shutter S2 once. The shutters S1 and S2 respectively transmit light during the "passage" period in FIG. 4 and block light during the "blocking" period in FIG. 4. Total of these "passage" and "blocking" periods corresponds to the period during which the wheels W1 and W2 each rotate once. Additionally, while the first shutter S1 transmits light, the second shutter S2 blocks light and each of the green light, the blue light and the red light passes through the first shutter S1 once. On the other hand, while the first shutter S1 is blocking light, the second shutter S2 transmit the excitation light. Therefore, while the wheels W1 and W2 rotate twice, the green light, the blue light, the red light, and the excitation light sequentially enter the light guide 14 once. The light entering the light guide 14 is guided by the light guide 14 itself and projected toward the object via the light distribution lens (not shown), located at the tip end of the video endoscope 1. Thus, the subject is sequentially and repeatedly irradiated by the green light, the blue light, the red light, and the excitation light.

When the subject is illuminated by the green light, the objective lens (not shown) forms an image of the object from the green light, near the imaging surface of the CCD 15. The period for which the object is illuminated by the green light corresponds to a "G accumulation" period for the CCD 15 (see FIG. 4). Charges accumulated in the CCD 15 during the "G accumulation" period are transmitted to the image signal processing circuit 24 as a G image signal during a "G transfer" period immediately following the "G accumulation" period. Then, the image signal processing circuit 24 generates image data (G image data) indicating an image of the object on the basis of the green light. When the object is illuminated by the blue light, the objective lens (not shown) forms an image of the object from the blue light, near the imaging surface of the CCD 15. The period for which the object is illuminated by the blue light corresponds to a "B accumulation" period for the CCD 15. Charges accumulated in the CCD 15 during the "B accumulation" period are transmitted to the image signal processing circuit 24 as a B image signal during a "B transfer" period immediately following the "B accumulation" period. The image signal processing circuit 24 then generates image data (B image data) indicating an image of the object on the basis of the blue light. When the object is illuminated by the red light, the objective lens (not shown) forms an image of the object from the red light, near the imaging surface of the CCD 15. The period for which the object is illuminated by the red light corresponds to an "R accumulation" period for the CCD 15. Charges accumulated in the CCD 15 during the "R accumulation" period are transmitted to image signal processing circuit 24 as an R image signal during an "R transfer" period immediately following the "R accumulation" period. The image signal processing circuit 24 then generates image data (R image data) indicating an image of the object on the basis of the red light. On the other hand, when the object is irradiated by the excitation light, the object emits autofluorescence. Thus, when the object is irradiated by the excitation light, the excitation light reflected by the object and the autofluorescence emitted from the object are incident on the objective lens (not shown). However, since the excitation light is blocked by the excitation light cut-off filter (not shown), an image of the object only from the autofluorescence is formed, near the imaging surface of the CCD 15. The period for which the object is irradiated by the excitation light corresponds to an "F accumulation" period for the CCD 15. Charges accumulated in the CCD 15 during the "F accumulation" period are transmitted to the image signal processing circuit 24 as an F image signal during an "F transfer" period immediately following the "F accumulation" period. The image signal processing circuit 24 then generates image data (F image data) indicating an image of the object on the basis of the autofluorescence. Thus, the image signal processing circuit 24 sequentially and repeatedly generates G image data, B image data, R image data and F image data.

Figure 5:
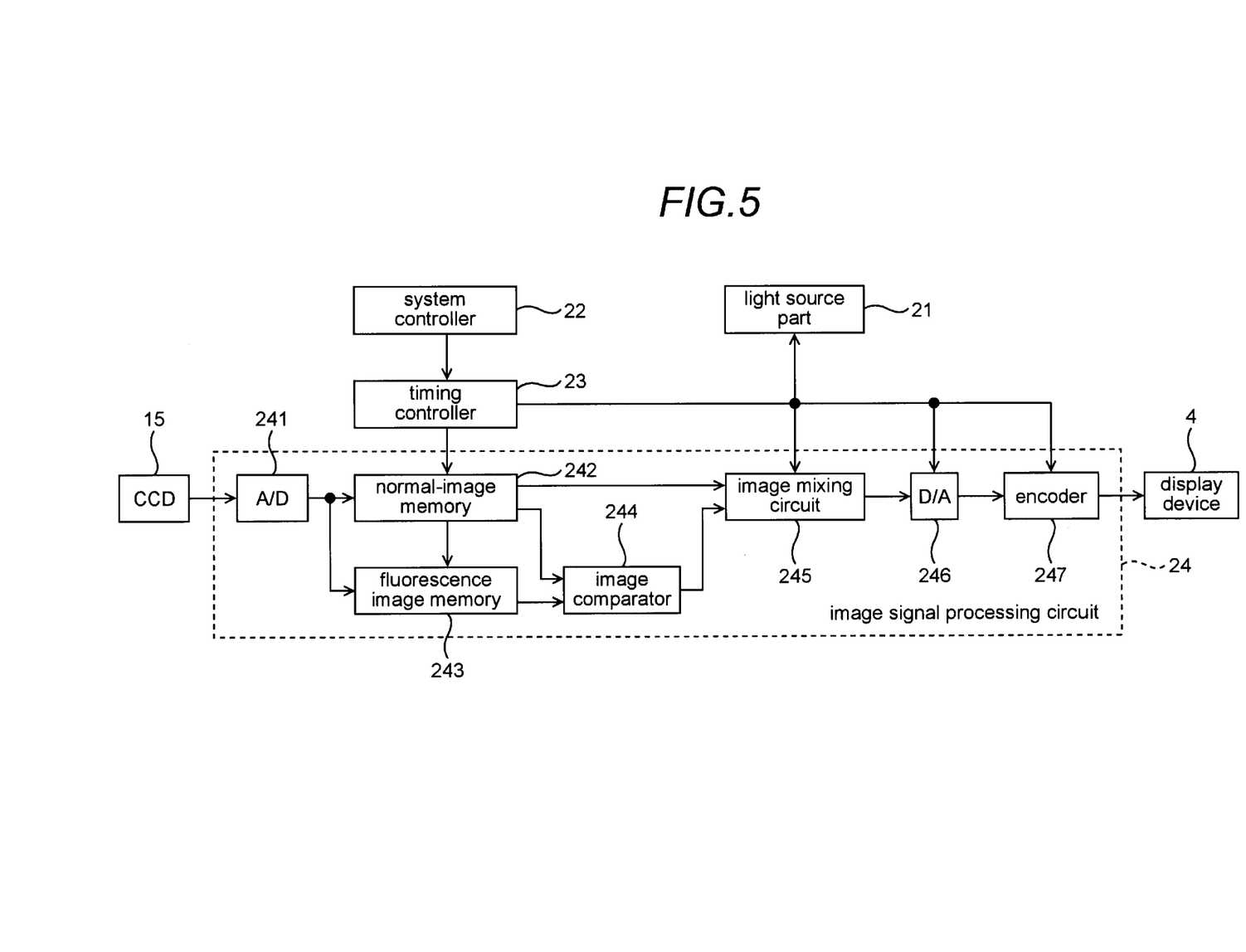
FIG. 5 is a block diagram showing the configuration of an image signal processing circuit.

The specifics of the image processing performed by the image signal processing circuit 24 will be described. FIG. 5 is a block diagram showing the configuration of the image signal processing circuit 24. As shown in this figure, the image signal processing circuit 24 has an A/D converter 241, a normal-image memory 242, a fluorescence image memory 243, and an image comparator 244. The A/D converter 241 is connected to the CCD 15, the normal-image memory 242 and the fluorescence image memory 243. The A/D converter 241 sequentially receives the G, B, R and F image signals output from the CCD 15, and analog-to-digital converts them to output the converted G, B, R, and F image data sequentially. Alternatively, the image signals output from the CCD 15 may be input to the A/D converter 241 after amplification. The normal-image memory 242 has storage areas corresponding to each of RGB colors of each pixel on a screen of the display device 4. On the other hand, the fluorescence image memory 243 has storage areas corresponding to pixels on the screen of the display device 4. Therefore, the normal-image memory 242 is capable of storing colored image data, while the fluorescence image memory 243 can store monochromatic image data. The normal-image memory 242 and the fluorescence image memory 243 are respectively connected to the timing controller 23. While the A/D converter 241 outputs the G, B, and R image data to the normal-image memory 242, each color of the image data is stored in corresponding storage areas in the normal-image memory 242 to generate the colored image data (normal-image data) indicating the object. On the other hand, when A/D converter 241 outputs the F image data, the fluorescence image memory 243 receives and stores the data as monochromatic image data (fluorescence data) indicating the object on the basis of the autofluorescence. The image comparator 244 respectively connected to the normal-image memory 242, the fluorescence image memory 243 and an image mixing circuit 245 receives the F image data from the fluorescence image memory 243, and extracts only the R image data from the normal-image data stored in the normal-image memory 242. The image comparator 244 further subtracts the R image data from the F image data to output specific image data. The R image data corresponds to monochromatic image data indicating the object on the basis of the red light, and thus corresponds to the reference image data. The image signal processing circuit 24 further has an image mixing circuit 245, a D/A converter 246 and an encoder 247, each of which is connected to the timing controller 23. The image mixing circuit 245 is connected to the normal-image memory 242 and the image comparator 244 respectively. The image mixing circuit 245 combines the normal-image data output from the normal-image memory 242 and the specific-image data output from the image comparator 244 to generate diagnostic image data. The D/A converter 246 is respectively connected to the image mixing circuit 245 and the encoder 247. The encoder 247 is further connected to the display device 4. The diagnostic image data output from the image mixing circuit 245 are then digital-to-analog converted by the D/A converter 246, and the encoder 247 adds a signal required to display image on the display device 4 to the converted analog diagnostic image signal. The diagnostic image signal output from the encoder 247 is transmitted to the display device 4, thereby displaying a diagnostic image on the screen of the display device 4 as a moving picture.

Figure 6:
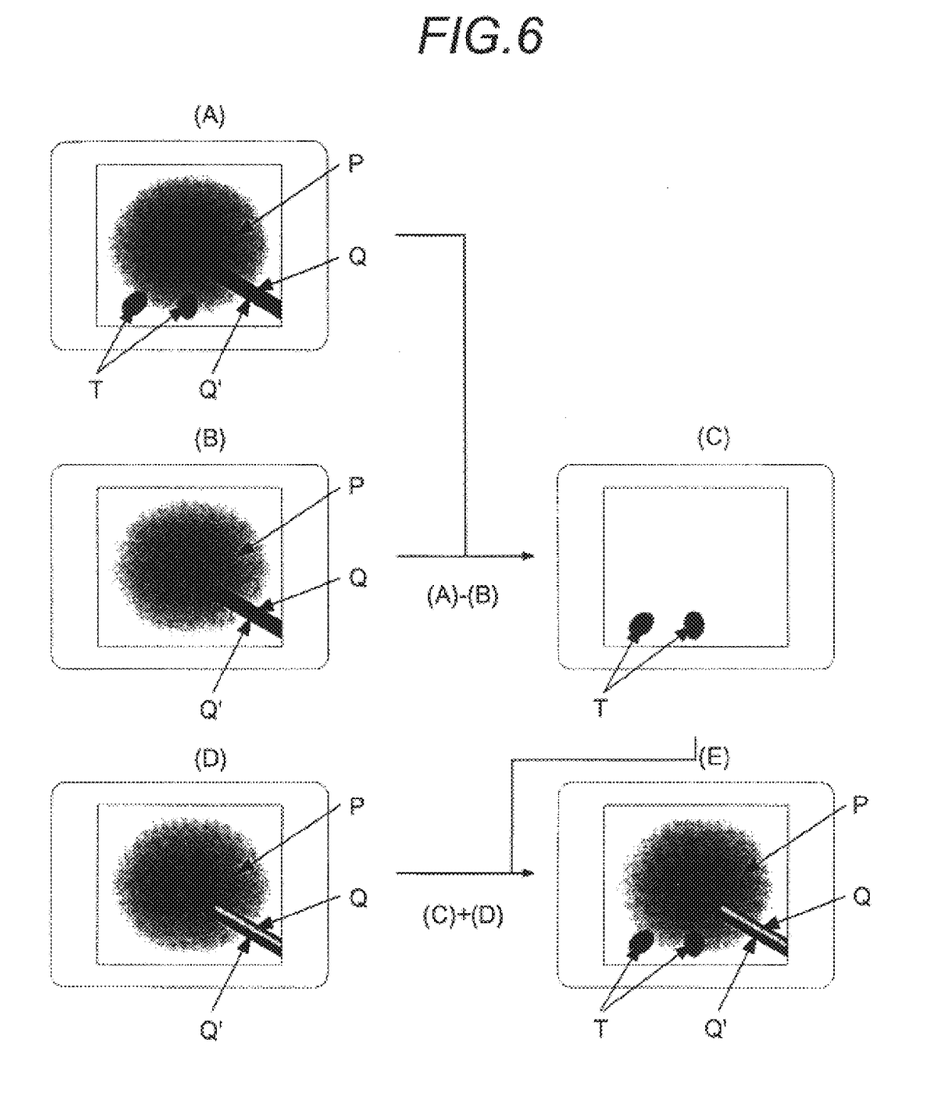
FIG. 6 is an explanatory representation showing a diagnostic image generating process.

The process of generating a diagnostic image executed by the image comparator 244 and the image mixing circuit 245 will be specifically described with reference to FIG. 6. FIG. 6A schematically shows an example of a fluorescence image resulting from the fluorescence image data stored in the fluorescence image memory 243, which is captured when the distal end of the video endoscope 1 is opposite a lumen within living body. In this fluorescence image, an interior P of the lumen, a forceps Q projecting from the forceps channel and its shadow Q', and a diseased portion T are all darkened. On the other hand, FIG. 6B schematically shows a reference image resulting from R image data (reference image data) extracted from normal-image data captured at the same time. In this reference image, the interior P of the lumen, the forceps Q, and its shadow Q' are darkened, but the diseased portion T, is not darkened. The image comparator 244 subtracts the luminance value of each pixel of the reference image data from the luminance value of the corresponding pixel of the fluorescence data after a predetermined process, to generate monochromatic image data (specific-image data) including only diseased portion T. FIG. 6C schematically shows a specific image resulting from the specific-image data. The image mixing circuit 245 combines the normal-image data stored in the normal-image memory 242 and the specific-image data generated by the image comparator 244 to generate diagnostic image data. FIG. 6E schematically shows a diagnostic image generated from the diagnostic image data. In other words, the image mixing circuit 245 superimposes the specific image shown in FIG. 6C upon the normal image shown in FIG. 6D to generate the diagnostic image shown in FIG. 6E. In the combining or superimposing, the image mixing circuit 245 sets the luminance value of a pixel in the normal-image data corresponding to the diseased portion T contained in the specific image to a luminance value indicative of a particular primary color (for example, blue). Thus, in the diagnostic image, diseased portion T is expressed in a particular color, over a colored image of the object. The operator can observe this diagnostic image to easily recognize the shape and position of diseased portion T. The diagnostic image and the normal image may be displayed side by side on the screen of the display device 4.

As described above, this video endoscope system uses the R image signal components in the normal-image data as the reference image data used to generate diagnostic image data. Thus, the light source part 21 repeatedly emits the green light, the blue light, the red light and the excitation light to enable the image signal process circuit 24 to generate moving diagnostic image data. Since red light is absorbed less by living tissue and blood than blue or green light, the R image signal components in the normal-image data are unlikely to be affected by the living tissue nor the blood, and are thus suited as reference image data. Further, since the light source part 21 is not required to emit a reference light only for the purpose of obtaining a reference image, the configuration of the optical system of the light source part 21 is simplified in comparison to prior art. More specifically, the excitation light in the conventional example shown in FIG. 8 travels to the light guide 87 through the three prisms 85, 88, and 91, while the excitation light in this embodiment shown in FIG. 2 travels to the light guide 14 through a single prism 213. Thus, the amount of the excitation light in this embodiment is attenuated less than in the prior art. Therefore, the video endoscope system of this embodiment enables the object to be irradiated by more intense excitation light. Accordingly, since autofluorescence of sufficient intensity is emitted from the object, this video endoscope system obtains clear fluorescence and diagnostic images. The simplified configuration of the light source part 21 also reduces the number of parts and the number of assembly steps required for manufacture, and facilitates the adjustment of the optical axis of each optical member, reducing product manufacturing costs still further. As shown in FIG. 3B, opening A in second wheel W2 of light source part 21 is longer along the circumference than the opening in second wheel 90 of the conventional example shown in FIG. 9B. When wheels W2 and 90 are compared on the assumption that they rotate at equal speed, the duration for which excitation light passes through the wheel W2 of this embodiment is longer than that for conventional wheel 90. Consequently, according to this embodiment, the period (F accumulation period) during which the autofluorescence accumulates in CCD 15 is set longer than in the prior art. Setting a longer F accumulation period results in clear fluorescence and diagnostic images.

Second Embodiment

Figure 7:
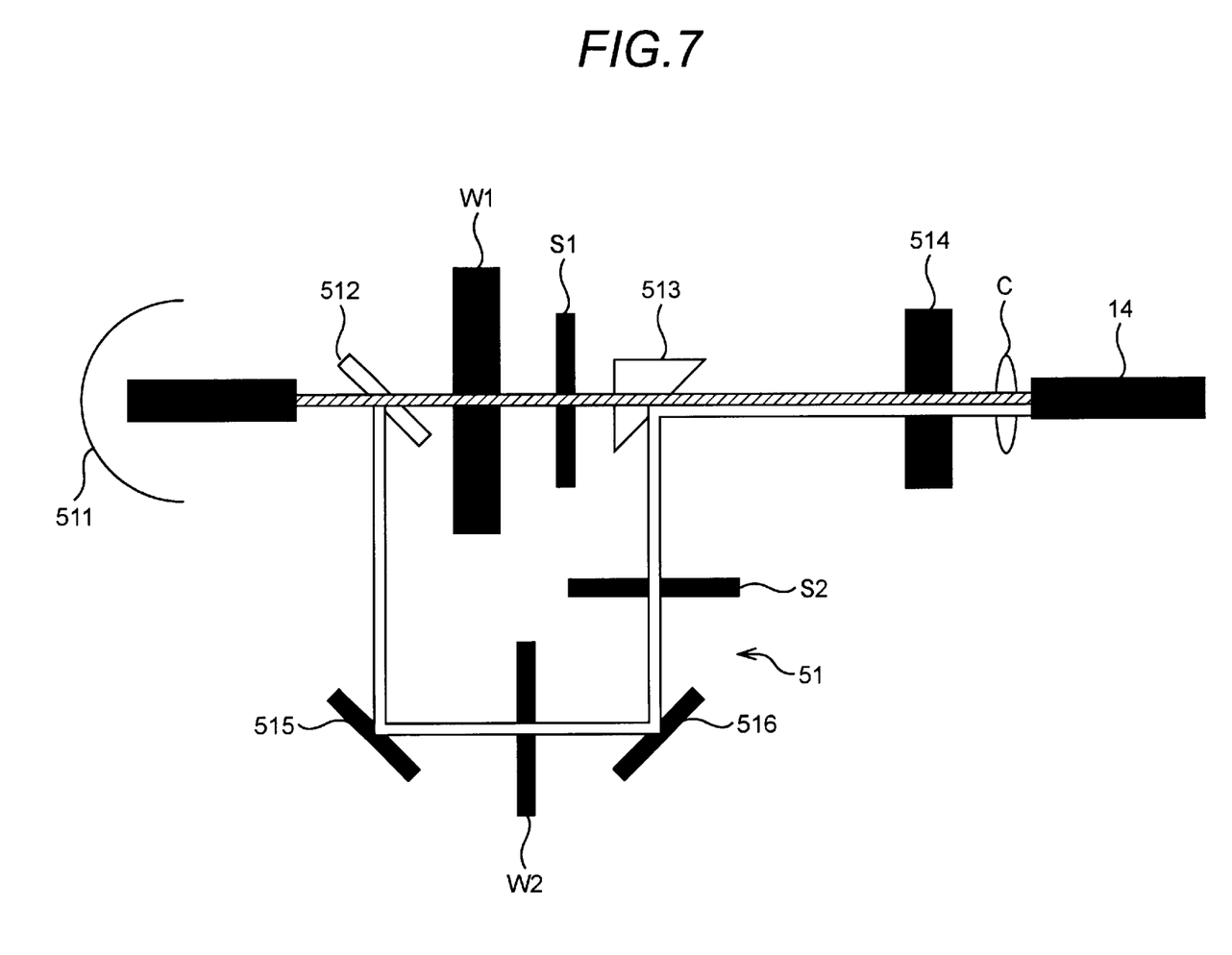
FIG. 7 is a schematic illustration showing the configuration of a light source device according to a second embodiment of the present invention.

A video endoscope system according to second embodiment is the same as the video endoscope device according to the first embodiment, except for the configuration of a light source part 51 of the external device 2. FIG. 7 is a schematic illustration showing the configuration of the light source part 51. As shown in this figure, the light source part 51 has a light source 511 for emitting collimated light containing components of the visible spectrum and a spectrum available as excitation light. The light source part 51 further has a dichroic mirror 512 disposed on the optical path of light emitted from the light source 511. The dichroic mirror 512 transmits only the visible spectrum components contained in the light emitted from light source 511 as white light, while reflecting the components of the spectrum available as excitation light. The excitation light reflected by the dichroic mirror 512 travels in a predetermined direction perpendicular to the path of the white light transmitted through the dichroic mirror 512. The dichroic mirror 512 corresponds to a separation device.

First wheel W1, first shutter S1, prism 513, diaphragm 514, and condenser lens C are arranged along the optical path of the white light transmitted through the dichroic mirror 512, in order. The first wheel W1 and the first shutter S1 are the same as in the first embodiment. Thus, the white light entering the first wheel W1 is sequentially and repeatedly converted into the green light, the blue light and the red light, which advance then to the first shutter S1. The green light, the blue light and the red light travel to the prism 513 only while the first shutter S1 allows the light to pass therethrough. The prism 513 has a UV reflection film deposited on its inclined surface to transmit visible light while reflecting excitation light. Thus, visible light the green light, the blue light and the red light entering the prism 513 is transmitted through prism 513 and then advances to the diaphragm 514. The diaphragm 514 adjusts amount of the incident green light, blue light and red light to proper quantity. The green light, the blue light and red light are then converged on the proximal end face of the light guide 14 by the condenser lens C.

On the other hand, a first mirror 515 is disposed on the optical path of the excitation light reflected by the dichroic mirror 512. The first mirror 515 reflects the incident excitation light so that the light travels parallel to and in the same direction as the white light transmitted through the dichroic mirror 512. The second wheel W2 and the second mirror 516 are arranged along the optical path of the excitation light reflected by the first mirror 515, in order. The second wheel W2 is the same as in the first embodiment. Thus, excitation light transmitted through the opening in the second wheel W2 then advances to the second mirror 516, which reflects the incident excitation light so that the optical path of the reflected excitation light orthogonally crosses, at the inclined surface of prism 513, to the optical path of the green light, the blue light and the red light having passed through the first shutter S1. The mirrors 515 and 516 correspond to a light introduction section. The second shutter S2 is disposed on the optical path between the second mirror 516 and the prism 513. The second shutter S2 is the same as in the first embodiment. The excitation light transmitted through the second shutter S2 is reflected by the prism 513, then travels through the same optical path as the green light, the blue light and the red light, finally entering the light guide 14.

The wheels W1 and W2 and the shutters S1 and S2 operate in the same manner as in the first embodiment.

Accordingly, the green light, the blue light, the red light and the excitation light are sequentially and repeatedly incident on the light guide 14. The video endoscope system of the second embodiment generates and displays diagnostic images in the same manner as the first embodiment.

The light source part 51 used in the video endoscope system according to the second embodiment has only one light source 511. Thus, the configuration of the light source part 51 is simpler than that including an excitation light source and a visible light source, reducing the number of parts and the number of assembly steps required in product manufacturing and facilitating the adjustment of the optical axis of each optical member. This reduces costs for manufacturing.

The video endoscope system of the present invention configured as described above has a simplified optical path system in the light source part for emitting the visible and excitation light used to obtain moving diagnostic images. This system allows the visible and excitation light to be applied to the subject while maintaining sufficient intensity and without significant attenuation in the optical path system, resulting in clear moving diagnostic images of the subject.

What is claimed is:

1. A video endoscope system comprising:
    a visible-light source for emitting visible light;
    an excitation light source for emitting excitation light that excites living tissue to cause autofluorescence, the excitation light source being arranged so that the emitted excitation light crosses, at a predetermined intersecting point, to an optical path of the visible light emitted from said visible-light source;
    a light guide for guiding the light to irradiate an object;
    an optical member disposed at said intersecting point to guide said visible light and said excitation light to said light guide along same optical path;
    a switching mechanism for switching between the visible light and the excitation light to introduce them into said optical member;
    an objective optical system for converging those components of light from a surface of the object irradiated with said light guide other than the excitation light to form an image of the surface of the object;
    an imaging device for picking up the image to convert it into an image signal; and
    a processor for controlling said switching mechanism to alternately and repeatedly introduce said visible light and said excitation light into the said light guide, generating normal-image data on the basis of a portion of the image signal corresponding to a period during which the visible light is introduced into said light guide, while generating fluorescence image data on the basis of a portion of the image signal corresponding to a period during which the excitation light is introduced into said light guide, obtaining reference image data from said normal-image data, extracting a diseased portion on the basis of the reference image data and said fluorescence image data, and superimposing the diseased portion on said normal-image data to generate diagnostic image data to be displayed as a moving picture.

2. A video endoscope system according to claim 1, further comprising a first wheel having a green filter transmitting green light, a blue filter transmitting blue light, and a red filter transmitting red light, along its circumference, the first wheel being rotated to sequentially insert the green filter, the blue filter, and the red filter into the optical path of said visible light; and
    wherein said processor generates the normal-image data from a part of the image signal corresponding to a period during which the green filter of said first wheel is inserted into the optical path, a part of the image signal corresponding to a period during which the blue filter of said first wheel is inserted into the optical path, and a part of the image signal corresponding to a period during which the red filter of said first wheel is inserted into the optical path.

3. A video endoscope system according to claim 2, wherein said processor obtains as the reference image data the part of the image signal corresponding to the period during which the red filter of said first wheel is inserted into the optical path.

4. A video endoscope system according to claim 1, further comprising a second wheel having an opening through which light passes, in an area of predetermined length extending along the circumference thereof, the second wheel being rotated to intermittently insert the opening into the optical path of said excitation light; and
    wherein said processor generates fluorescence image data on the basis of the portion of the image signal corresponding to the period during which the opening of said second wheel is inserted into the optical path.

5. A video endoscope system according to claim 1, further comprising a display device for displaying the moving picture in accordance with the image data generated by said processor.

6. A video endoscope system comprising:
    a light source for emitting light containing components of spectrum of the visible light and components of a spectrum of excitation light that excites living tissue to cause autofluorescence;
    a light guide for guiding the light to illuminate an object;
    a separation device for separating the light emitted from the light source into the visible light and the excitation light;
    a light-guiding optical system for separately guiding the visible light and the excitation light obtained by said separation device so that they cross each other at a predetermined intersecting point;
    an optical member disposed at said intersecting point to guide the visible light and the excitation light to said light guide;
    a switching mechanism for switching between the visible light and the excitation light to introduce them into said optical member;
    an objective optical system for converging those components of light from a surface of the object irradiated with said light guide other than the excitation light to form an image of the surface of the object;
    an imaging device for picking up the image to convert it into an image signal; and
    a processor for controlling said switching mechanism to alternately and repeatedly introduce said visible light and said excitation light into said light guide, generating normal-image data on the basis of a portion of the image signal corresponding to a period during which the visible light is introduced into said light guide, while generating fluorescence image data on the basis of a portion of the image signal corresponding to a period during which the excitation light is introduced into said light guide, obtaining reference image data from said normal-image data, extracting a diseased portion on the basis of the reference image data and said fluorescence image data, and superimposing the diseased portion on said normal-image data to generate diagnostic image data to be displayed as a moving picture.

* * * * *